United States Patent [19]

Redfern

[11] 4,402,690

[45] Sep. 6, 1983

[54] HIGH ABSORBENCY, CONTOURED, REUSABLE DIAPER

[76] Inventor: Robin Redfern, 6737 W. Costa Brave Rd., Las Vegas, Nev. 89102

[21] Appl. No.: 199,279

[22] Filed: Oct. 21, 1980

[51] Int. Cl.³ .............................................. A41B 13/02
[52] U.S. Cl. ................................................... 604/391
[58] Field of Search .................. 128/284, 287, 290 R; 604/365–367, 370–372, 374, 378, 381, 385, 391

[56] References Cited

U.S. PATENT DOCUMENTS

| | | | |
|---|---|---|---|
| 2,500,255 | 3/1950 | Lee | 128/284 |
| 2,627,858 | 2/1953 | Miller | 128/287 |
| 2,675,805 | 4/1954 | Trimble | 128/284 |
| 2,695,025 | 11/1954 | Andrews | 128/287 |
| 2,717,437 | 9/1955 | DeMestral | 128/DIG. 15 |
| 2,866,459 | 12/1958 | Sobelson | 128/284 |
| 3,081,772 | 3/1963 | Brooks et al. | 128/287 |
| 3,089,494 | 5/1963 | Schwartz | 128/284 |
| 3,141,461 | 7/1964 | Farris | 128/284 |
| 3,150,664 | 9/1964 | Noel | 128/287 |
| 3,359,980 | 12/1967 | Rosenblatt | 128/287 |
| 3,618,608 | 11/1971 | Brink | |
| 3,996,936 | 12/1976 | Widlund et al. | 128/287 |
| 4,047,531 | 9/1977 | Karami | 128/287 |
| 4,050,462 | 9/1977 | Woon et al. | 128/290 R |

*Primary Examiner*—C. Fred Rosenbaum
*Attorney, Agent, or Firm*—Saidman, Sterne & Kessler

[57] ABSTRACT

Symmetrical ends of a diaper are fastened by the use of hook and pile fasteners which are mounted on wings that extend laterally from the main diaper body. The hook sections of the fastener are substantially longer than the pile sections and face outwardly of the diaper so as not to irritate an infant's skin yet allow a large degree of adjustability. Elastic strips are sewn to the main body in the vicinity of the leg openings to make the diaper hug the legs of the infant. The diaper is composed of a plurality of layers of material which channel moisture to a central layer which is not easily contacted either from the inside or outside of the diaper. Quilt stitches can also be included to dissipate moisture along the entire length of the diaper.

12 Claims, 5 Drawing Figures

HIGH ABSORBENCY, CONTOURED, REUSABLE DIAPER

BACKGROUND OF THE INVENTION

1. Field of the Invention

This invention relates to diapers and particularly to diapers which are adjustable to fit a variety of infants and are also reusable.

2. Discussion of Related Art

Diapers have been increasingly improved over the last decades. Initially, a diaper consisted of a panel of absorbant material formed in a rectangle. The diaper was appropriately folded and pinned to an infant. These diapers have a great many deficiencies including a tendency to cause diaper rash due to excessive moisture contact with the infant's skin and the tendency to leak due to inadequate sealing between the diaper and the infant.

One early development of a diaper can be seen with respect to U.S. Pat. No. 2,627,858 issued to Miller in February 1953. The Miller diaper is produced from a disposable material and includes longitudinally disposed tape on opposite edges to hold the diaper on the infant. The diaper is composed of a plurality of layers of material and is contoured to fit an infant. However, the tapes of Miller do not allow for adjustment of the diaper size. Also, the specific contour of the diaper reduces the absorbency by removing a large amount of material in the diaper front.

U.S. Pat. No. 2,866,459 issued Dec. 30, 1958 to Sobelson shows an infant's diaper composed of a rectangular sheet folded upon itself and stitched at its edges to form a tubular body. A plurality of longitudinally extending elastic stitches are disposed along the body to help it conform to the shape of an infant. However, the number of stretch stitches used in Sobelson would tend to pinch a baby's skin. Also, Sobelson requires safety pins to hold the diaper in place.

U.S. Pat. No. 3,081,772 issued Mar. 19, 1963 to Brooks et al shows a diaper made from a plurality of plies of moisture resistant plastic material having an inwardly projecting ridge of hourglass configuration provided with a strip of resilient material located between the plies of plastic. A hook and pile fastener is located on opposite ends of the diaper to hold it in place on an infant. The Brooks et al device is designed in a manner which does not allow great adjustability. Also, the use of disposable materials by Brooks et al makes use of that diaper exceedingly expensive.

U.S. Pat. No. 3,141,461 issued July 21, 1964 to Farris; U.S. Pat. No. 3,150,664 issued Sept. 29, 1964 to Noel; and U.S. Pat. No. 3,618,608 issued Nov. 9, 1971 to Brink all show diaper constructions utilizing hook and pile fasteners for maintaining the diaper in position on an infant. Each of these patents is difficult to use and cannot easily be placed in proper position on an infant.

OBJECTS OF THE INVENTION

One object of the present invention is to provide a diaper which can be laundered so as to enable its reuse thereby reducing the total cost of diaper usage during infancy.

Another object of the present invention is to provide a reusable diaper which is contoured to conform to an infant's shape yet is not unduly constricting in a manner to cause skin irritation or other discomfort.

A further object of the present invention is to provide a reusable diaper which can easily be adjusted to fit infants of various sizes or to fit one infant as it grows larger.

Another object of the present invention is to provide a reusable diaper which channels moisture away from an infant's skin thereby reducing the incidence of diaper rash.

SUMMARY OF THE INVENTION

In accordance with the above and other objects of the invention, my diaper comprises a main body having first and second spaced ends each of which contains a pair of opposed, laterally extending wings. An attachment device in the form of a hook and pile fastener such as is sold under the trademark VELCRO ® is connected to the wings for holding the wings in overlapping position, thus holding the diaper on the infant. The use of wings in this manner allows the diaper to have great adjustability since the amount of overlap can be controlled while not severely restricting the size of the leg openings partially formed thereby. Also, elastic stretch cords are sewn into the diaper along the area of the leg openings to allow the leg openings to automatically adjust to the size of an infant's leg and also to provide a snug fit between the diaper and the infant's legs.

An additional feature of the invention is provided by the disposition of the hook elements of the hook and pile fastener on the outer surface of the diaper, such that the hook elements face outwardly and do not irritate the infant's skin. The pile elements face inwardly and, accordingly, even if they contact the infant's skin no irritation will be caused. Furthermore, the hook elements are substantially greater in length than the pile elements thus allowing the diaper to be easily adjusted.

An additional feature of the invention resides in the use of a plurality of layers of dissimilar material for channeling moisture away from the skin of the infant. Each layer comprises one or more plies of moisture absorbant or nonabsorbant material. The innermost layer of the diaper rests against the infant's skin and thus must be soft but non-moisture absorbant. Immediately adjacent to that layer, a thick padding layer of nonabsorbant material is provided to channel the moisture to an inner absorbant layer. In this manner, the moisture is kept at a distance from the infant's skin. Similarly, an outer padding layer is used to insulate the outermost layer of the diaper from moisture contained in the central layer.

Also, quilt stitches extending longitudinally of the diaper main body are provided such that moisture can be channeled longitudinally of the diaper thereby increasing the diaper's moisture absorbing capabilities.

BRIEF DESCRIPTION OF THE DRAWINGS

Other objects and advantages of the invention will become subsequently apparent as the invention becomes more fully understood with reference to the accompanying drawings in which like references characters represent identical or similar components throughout the several views, wherein.

DESCRIPTION OF THE PREFERRED EMBODIMENT

Figure 1:
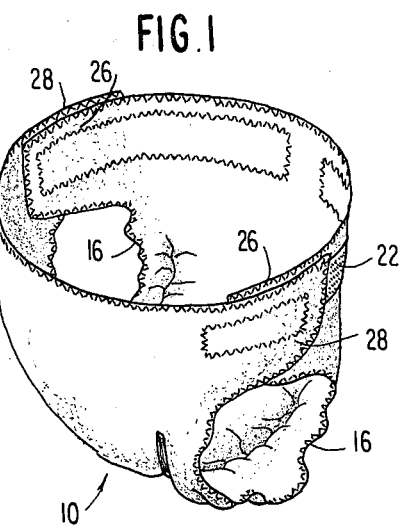
FIG. 1 is a perspective view of the diaper with opposite ends attached to conform to an infant's physiology.
Figure 2:
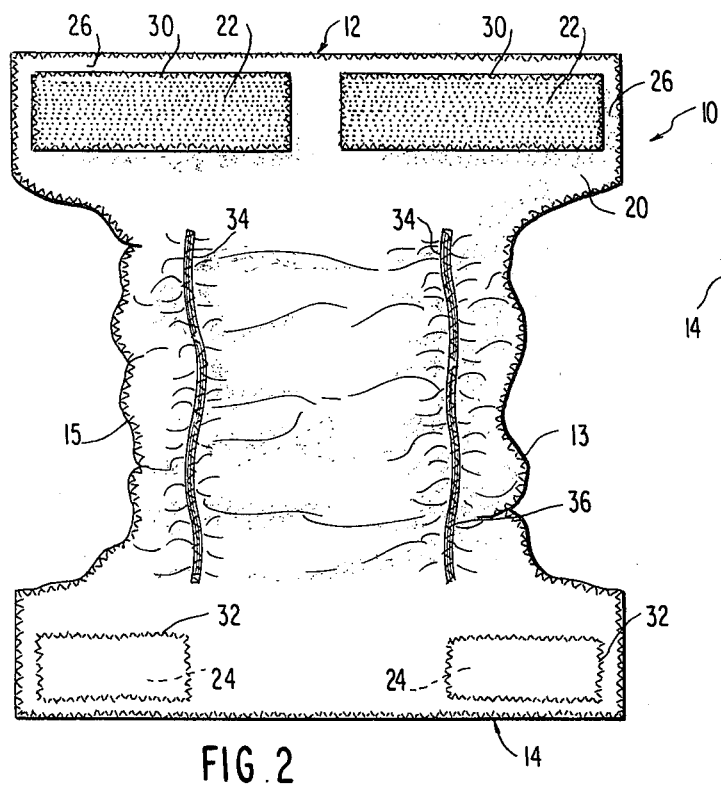
FIG. 2 is a plan view of the outside of the diaper showing the elastic cords in their relaxed state.
Figure 3:
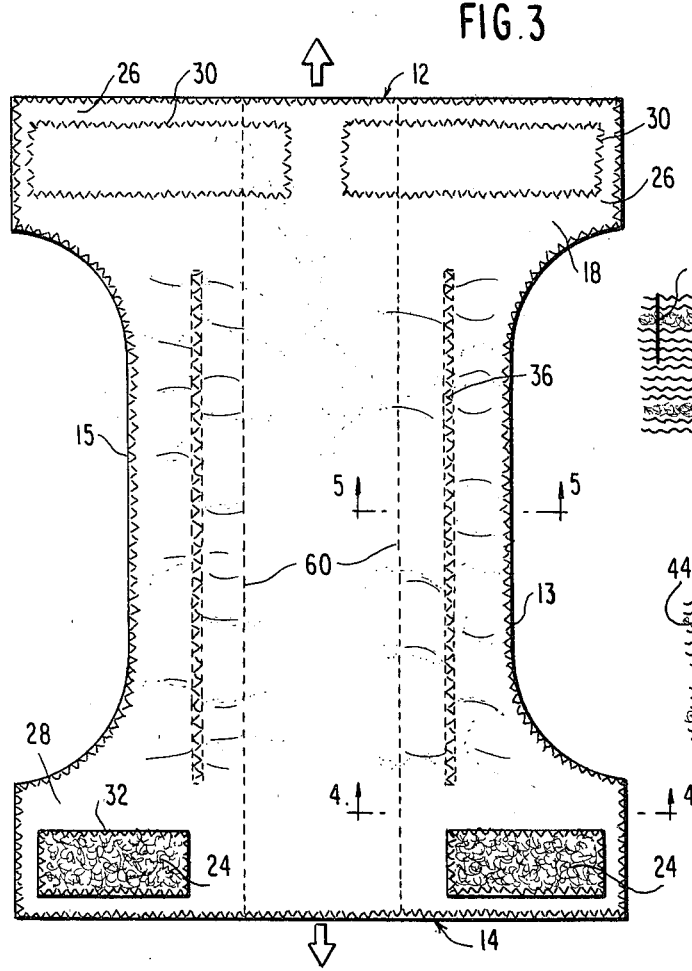
FIG. 3 is a plan view of the inside of the diaper showng the elastic cords in their stretched state.

Now with reference to the drawings, a diaper incorporating the principles and concepts of the present invention and generally referred to by the reference numeral 10 will be described in detail. With specific reference to FIGS. 1, 2 and 3, it can be seen that the diaper comprises a main body portion having first and second spaced ends 12 and 14 with substantially linear side walls 13 and 15 which form the leg openings 16. The leg openings 16 are also partially defined by the wing sections 26 which extend laterally in opposite directions from the first end 12 and the wing sections 28 which extend laterally in opposite directions from the second end 14. As is evident from FIGS. 1-3, the diaper is curved about a transverse axis and the pairs of wings 26 are overlapped by wings 28 such that the ends 12 and 14 align to form a complete loop to encircle the midsection of an infant. At the same time, such curvature of the diaper causes the sides 13 and 15 to curve into a circle to form the leg openings. By merely adjusting the overlap of the wings 26, 28, the diaper can be adjusted to accommodate infants of various size. While this adjustment does affect the size of the opening 16, no additional adjustment for the leg openings 16 is necessary by virtue of the use of a pair of elastic strips 34 which, as seen in FIGS. 2 and 3, are sewn to the fabric in a position spaced from the associated edge 13 or 15. The elastic strips are sewn in the stretched position as shown in FIG. 3 by use of a zigzag stretch stitch 36. When the elastic strips 34 are allowed to relax, the sides of the diaper are gathered as showing FIG. 2. This causes the leg openings 16, when formed, to cradle the infant's legs in a manner which provides a sealing effect. The elastic strips 34 also serve to allow the leg opening 16 to vary in size sufficiently to accommodate various sized infants. It should be noted that the elastic strips 34 are sewn to the outside surface of the diaper as shown in FIG. 2. This produces a gathering effect on the inside of the diaper when the strips are relaxed. This gathering on the inner surface of the diaper is soft to the touch and thus will not irritate the infant's skin. The cushioning effect is further enhanced by the fact that elastic strips 34 are spaced from the sides 13, 15 thus providing padding on either side of the elastic strip preventing pinching or skin irritation.

The wings 26 and 28 are held in overlapping disposition by the use of hook and pile fasteners such as are sold under the name VELCRO®. These fasteners include relatively hard, stiff hook sections 22 affixed to the end 12 of the diaper and pile sections 24 affixed to end 14 of the diaper. It should be noted that the hook sections 22 are affixed to the outer surface 20 of the diaper to face outwardly therefrom, while the pile sections 24 are affixed to the inner surface 18 to face inwardly. Thus, when the wings 26 and 28 overlap as shown in FIG. 1, any hooks not in contact with the associated pile sections will face outwardly and therefore will not contact the infant's skin. Any pile which does not contact a portion of associated hook section can touch the infant's skin but will not cause irritation.

Also, it will be noted that each of the hook sections 22 are substantially longer than each of the pile sections 24. The hook sections extend from approximately the lateral center of the diaper to the terminal ends of the wings, while the pile sections only cover a portion slightly greater than the associated wings, or an area approximately half that of the hook sections. This allows a maximum amount of adjustability for the diaper. Each pile section can simply be moved across the associated hook section to provide the adjustment. Even though contact of the soft pile sections with an infant's skin is much less likely to cause irritation than similar contact with the hard hook sections, such contact of either section with the infant's skin should preferably be avoided. Thus, the size of the pile sections is reduced relative to size of the hook sections, thereby reducing the probability of any contact between the pile sections and the infant.

It is also noted that as shown on the drawings the hook sections 22 are affixed to the diaper by use of stitches 30 and the pile sections 24 are affixed by use of stitches 32. While sewing the hook and pile sections to the diaper in this manner is the preferred form of attachment, any other attachment device may also be used, as desired.

Figure 4:
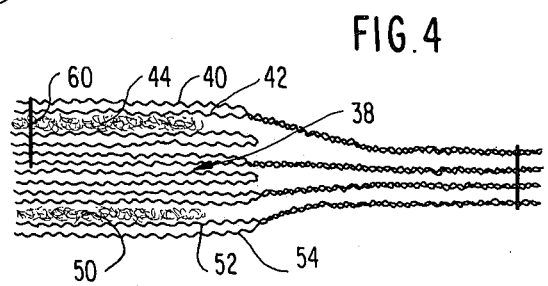
FIG. 4 is a transverse sectional view taken substantially along a plane passing through section line 4—4 of FIG. 3.
Figure 5:
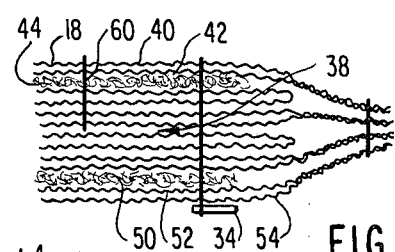
FIG. 5 is a transverse sectional view taken substantially along a plane passing through section line 5—5 of FIG. 3.

FIGS. 4 and 5 show cross-sectional views of the diaper to illustrate the material from which the diaper is preferably formed. The diaper is designed to channel moisture from the infant away from the inside surface 18 toward a central absorbant layer 38. The inner layer preferably comprises two plies 40 and 42 of cotton material or cotton gauze. This layer is loosely woven and allows moisture to pass readily therethrough. Immediately adjacent the inner layer is a quantity of padding 44 which can be made of polyester blend batting or any other suitable nonabsorbant padding. Padding 44 serves to provide substantial separation between the inner layer plies 40 and 42 and the central layer 38. Consequently, moisture which passes through the inner layer and through the padding 44 will be maintained at a distance from the inner layer thus reducing the possibility of skin irritation caused by constant contact with moisture laden material.

The central layer 38 can comprise a plurality of plies of cotton or cotton gauze material. As shown, seven plies are disposed therein. Alternatively, the central layer 38 could be made from heavy cotton or cotton blend terrycloth to provide superior absorbing capability. Immediately adjacent the central absorbing layer 38 is another layer of polyester blend batting 50. Covering batting 50 is an outer layer composed of two plies 52 and 54. The plies 52 and 54 are kept dry to the touch by the batting 50 which insulates the outer layer from the moisture contained in central layer 38. Both plies 50 and 54 can be cotton or cotton gauze material similar to the inner plies 40 and 42. Alternatively, ply 52 can be a water impervious material such as plastic which helps insure that no moisture will seep from the diaper and eliminates the need for the use of plastic pants. Ply 54 can be a flannel material which is soft to the touch and may contain a pleasing design, thus eliminating the need for any covering garments on the infant.

Another feature of the diaper 10 is the inclusion of a plurality of longitudinally extending stitch lines 60 which form a quilt pattern in the diaper. The stitch lines 60 can be, preferably, of a lock stitch type to inhibit their unraveling. The purpose of the stitch lines 60 is to provide a path along which moisture can flow to be dissipated throughout the entire diaper central layer 38. In this manner, the absorbant qualities of the diaper are enhanced. The stitches of stitch lines 60 can extend entirely through the diaper (not shown) or can merely extend through the innermost layers of the diapers as shown in FIG. 5. The purpose for not extending the stitches through the entire diaper is to prevent a wicking effect which would draw moisture to the outer plies 50 and 52. This is especially significant if ply 52 is to be made of a moisture impervious material since the stitch holes through that material would provide a means through which moisture could escape, thus negating the beneficial effect of the moisture impervious material.

The material from which the inner ply 40 and the outer ply 54 is to be made is optional and can include any of a variety of materials which are soft to the touch and can permit moisture to pass through. Cotton, cotton gauze and flannel are merely examples of such materials, with other similar materials being readily obvious to one of ordinary skill in the art.

As can be understood from the foregoing, the diaper 10 provides a soft, gentle feel to the infant and to one holding the infant by virtue of the inner and outer soft plies 40 and 54, yet is highly absorbant and effective in use. The diaper can be easily adjusted to a plurality of waist positions to accommodate virtually any infant. This single adjustment combined with the elastic band and the leg openings allows a parent to clothe their infant in a comfortable protective garment with a minimum of effort. When soiled, the diaper can be quickly and easily removed from the infant and washed in a standard washing machine. The fabrics from which the diaper is made are durable, long-lasting fabrics allowing the diaper to be reused many times, thus reducing the total cost of diapering a child during its infancy.

Obviously, numerous modifications and variations of the present invention are possible in light of the above teachings. Therefore, it is to be understood that within the scope of the appended claims, the invention may be practiced otherwise than as specifically described herein.

I claim as my invention:

1. A reusable diaper for children comprising:
   a main body having inwardly and outwardly facing surfaces, a first longitudinal end, a second longitudinal end, a first side edge and a second side edge;
   a first pair of oppositely directed laterally extending wings formed on said first end;
   a second pair of oppositely directed laterally extending wings formed on said second end and adapted to overlap said first pair of wings;
   hook and pile fastener means connected to said first and second pairs of wings and comprising a hook section and a pile section for maintaining said wings in overlapped disposition to form said diaper to the torso of an infant;
   wherein said hook section is disposed on said outwardly facing surface of said first pair of wings and said pile section is disposed on said inwardly facing surface of said second pair of wings; and
   elastic stretch means attached longitudinally of said body for gathering portions of said body about the legs of an infant;
   wherein said hook section is substantially greater in length than said pile section, and
   wherein said elastic stretch means comprises two elastic strips attached to the outer surface of said main body in a position substantially parallel to and spaced laterally from said first and second side edges for providing padding on both sides of each elastic strip.

2. The invention as defined in claim 1 wherein said main body and said first and second paris of wings are formed in a unitary construction from a plurality of layers comprising plies of dissimilar materials.

3. The invention as defined in claim 2 wherein said layers include an inner layer of soft, nonabsorbent material for contacting an infant's skin.

4. The invention as defined in claim 3 wherein said layers include a central layer of highly absorbent material.

5. The invention as defined in claim 4 and further including thick nonabsorbent inner padding layer disposed between said central layer and said inner layer for channeling moisture from said inner layer to said central layer.

6. The invention as defined in claim 5 and further including an outer layer of nonabsorbing material and a thick nonabsorbing outer padding layer disposed between said central layer and said outer layer for insulating said outer layer from moisture contained in said central layer.

7. A diaper for children comprising:
   a main body having inwardly and outwardly facing surfaces, a first longitudinal end, a second longitudinal end, a first side edge and a second side edge;
   a first pair of oppositely directed laterally extending wings formed on said first end;
   a second pair of oppositely directed laterally extending wings formed on said second end and adapted to overlap said first pair of wings;
   hook and pile fastener means connected to said first and second pairs of wings and comprising a hook section and a pile section for maintaining said wings in overlapped disposition to form said diaper to the torso of an infant;
   wherein said hook section is disposed on said outwardly facing surface of said first pair of wings and said pile section is disposed on said inwardly facing surface of said second pair of wings; and
   elastic stretch means attached longitudinally of said body for gathering portions of said body about the legs of an infant;
   wherein said main body and said first and second pairs of wings are formed in a unitary construction from a plurality of layers comprising plies of dissimilar materials;
   wherein said layers include an inner layer of soft, nonabsorbent material for contacting an infant's skin;
   wherein said layers include a central layer of highly absorbent material; and
   further including a thick nonabsorbent inner padding layer disposed between said central layer and said inner layer for channeling moisture from said inner layer to said central layer; and
   an outer layer of nonabsorbing material and a thick nonabsorbing outer padding layer disposed between said central layer and said outer layer for insulating said outer layer from moisture contained in said central layer
   and further including quilt stitches running longitudinally of said main body for channeling moisture along said body.

8. The invention as defined in claim 7 wherein said quilt stitches extend only between said inner layer, said inner padding layer and said central layer.

9. The invention as defined in claim 8, wherein said outer layer includes one ply of moisture impervious material.

10. A diaper for children comprising:

a main body having inwardly and outwardly facing surfaces, a first longitudinal end, a second longitudinal end, a first side edge and a second side edge;

a first pair of oppositely directed laterally extending wings formed on said first end;

a second pair of oppositely directed laterally extending wings formed on said second end and adapted to overlap said first pair of wings;

hook and pile fastener means connected to said first and second pairs of wings and comprising a hook section and a pile section for maintaining said wings in overlapped disposition to form said diaper to the torso of an infant;

wherein said hook section is disposed on said outwardly facing surface of said first pair of wings and said pile section is disposed on said inwardly facing surface of said second pair of wings; and elastic stretch means attached longitudinally of said body for gathering portions of said body about the legs of an infant;

wherein said main body and said first and second pairs of wings are formed in a unitary construction from a plurality of layers comprising plies of dissimilar materials;

wherein said layers include an inner layer of soft, nonabsorbent material for contacting an infant's skin;

wherein said layers include a central layer of highly absorbent material; and further including a thick nonabsorbent inner padding layer disposed between said central layer and said inner layer for channeling moisture from said inner layer to said central layer; and an outer layer of nonabsorbing material and a thick nonabsorbing outer padding layer disposed between said central layer and said outer layer for insulating said outer layer from moisture contained in said central layer wherein said central layer includes at least one ply of terrycloth material.

11. A diaper for children comprising:

a main body having inwardly and outwardly facing surfaces, a first longitudinal end, a second longitudinal end, a first side edge and a second side edge;

a first pair of oppositely directed laterally extending wings formed on said first end;

a second pair of oppositely directed laterally extending wings formed on said second end and adapted to overlap said first pair of wings;

hook and pile fastener means connected to said first and second pairs of wings and comprising a hook section and a pile section for maintaining said wings in overlapped disposition to form said diaper to the torso of an infant;

wherein said hook section is disposed on said outwardly facing surface of said first pair of wings and said pile section is disposed on said inwardly facing surface of said second pair of wings; and elastic stretch means attached longitudinally of said body for gathering portions of said body about the legs of an infant;

wherein said main body and said first and second pairs of wings are formed in a unitary construction from a plurality of layers comprising plies of dissimilar materials;

wherein said layers include an inner layer of soft, nonabsorbent material for contacting an infant's skin;

wherein said layers include a central layer of highly absorbent material; and further including a thick nonabsorbent inner padding layer disposed between said central layer and said inner layer for channeling moisture from said inner layer to said central layer; and an outer layer of nonabsorbing material and a thick nonabsorbing outer padding layer disposed between said central layer and said outer layer for insulating said outer layer from moisture contained in said central layer wherein said inner layer includes a plurality of plies of cotton gauze.

12. The invention as defined in claim 9 wherein said outer layer further includes a panel of flannel material covering said ply of moisture impervious material.

* * * * *